(12) United States Patent
Tuloup et al.

(10) Patent No.: US 6,228,350 B1
(45) Date of Patent: May 8, 2001

(54) METHOD OF DEPIGMENTING AND/OR BLEACHING SKIN AND/OR BODY HAIR OR HEAD HAIR

(75) Inventors: Remy Tuloup, Paris; Michel Philippe, Wissous, both of (FR)

(73) Assignee: L'Oreal, Paris (FR)

(*) Notice: Subject to any disclaimer, the term of this patent is extended or adjusted under 35 U.S.C. 154(b) by 0 days.

(21) Appl. No.: 09/489,840

(22) Filed: Jan. 24, 2000

(30) Foreign Application Priority Data

Jan. 27, 1999 (FR) .................................................. 99 00882

(51) Int. Cl.$^7$ ............................. A61K 7/135; A61K 7/00; A61K 31/15
(52) U.S. Cl. ............................. 424/62; 424/401; 514/640
(58) Field of Search ...................... 424/401, 62

(56) References Cited

U.S. PATENT DOCUMENTS

| 4,762,705 | 8/1988 | Rubin | 424/85 |
|---|---|---|---|
| 4,816,487 | 3/1989 | Schewe et al. | 514/640 |
| 5,702,710 | * 12/1997 | Charpentier et al. | 424/401 |

FOREIGN PATENT DOCUMENTS

| 41 16 123 | 11/1992 | (DE) . |
| 2 237 739 | 5/1991 | (GB) . |
| 89 00621 | * 5/1991 | (NL) . |
| 8 900 621 | 5/1991 | (NL) . |
| WO 95/01157 | 1/1995 | (WO) . |
| 95 01157 | * 1/1995 | (WO) . |

* cited by examiner

Primary Examiner—Thurman K. Page
Assistant Examiner—Blessing Fubara
(74) Attorney, Agent, or Firm—Oblon, Spivak, McClelland, Maier & Neustadt, P.C.

(57) ABSTRACT

The use, in a topical cosmetic composition, or for the manufacture of a topical dermatological composition, intended for depigmenting and/or bleaching human skin, body hair or head hair, of at least one compound comprising a phenyloxime fragment.

13 Claims, No Drawings

METHOD OF DEPIGMENTING AND/OR BLEACHING SKIN AND/OR BODY HAIR OR HEAD HAIR

BACKGROUND OF THE INVENTION

1. Field of the Invention

The present invention relates to a method of using, in a topical cosmetic composition, or for the manufacture of a topical dermatological composition, at least one compound comprising a phenyloxime fragment depigmenting and/or bleaching human skin, body hair or head hair.

2. Description of the Background

The color of human skin depends on various factors and in particular on the seasons of the year, race and sex, and it is mainly determined by the nature and concentration of melanin produced by the melanocytes. Melanocytes are specialized cells which synthesize melanin, via specific organelles, the melanosomes. In addition, at various periods in their life, certain individuals develop darker and/or more colored marks on the skin, and more especially on the hands, making the skin non-uniform. These marks are also due to a large concentration of melanin in the keratinocytes located at the surface of the skin.

Similarly, the color of body hair and head hair is due to melanin, and when the body hair or head hair is dark, certain individuals wish to make them lighter. This is particularly advantageous for body hair which is less visible when it is light than when it is dark.

The substances most commonly used as depigmenting agents are, more particularly, hydroquinone and its derivatives, in particular its ethers such as hydroquinone monomethyl ether and monoethyl ether. Unfortunately, although these compounds have a certain level of efficacy, they are not free of side effects on account of their toxicity, which can make them problematic or even hazardous to use. This toxicity arises from the fact that they intervene in fundamental mechanisms of melanogenesis by killing cells which then create the risk of disrupting their biological environment and consequently oblige the skin to remove them by producing toxins.

Thus, hydroquinone is a compound which is particularly irritant and cytotoxic to melanocytes, and its total or partial replacement has been envisaged by many authors.

The use of harmless topical depigmenting substances which have good efficacy is most particularly desired in order to treat regional hyperpigmentations caused by melanocyte hyperactivity, such as idiopathic melasmas occurring during pregnancy ("pregnancy mask" or chloasma) or during oestro-progestative contraception, localized hyperpigmentations caused by hyperactivity and proliferation of benign melanocytes, such as senile pigmentation marks known as actinic lentigo, accidental hyperpigmentations or depigmentations, which may be due to light-sensitization or to post-lesional cicatrization, as well as certain leukodermias, such as vitiligo. For the latter pigmentation conditions (it being possible for cicatrizations to result in a scar giving the skin a whiter appearance, and leukodermias), failing the ability to repigment the damaged skin, the approach finally adopted is to depigment the regions of residual normal skin in order to give the skin as a whole a uniform white shade.

Thus, a need exists for a novel agent for bleaching human skin, body hair and/or head hair, which acts as effectively as the known agents but does not have their drawbacks, i.e. which is non-irritant, non-toxic and/or non-allergenic to the skin and is stable in a composition.

SUMMARY OF THE INVENTION

The inventors have now discovered, unexpectedly, that compounds comprising a phenyloxime fragment have depigmenting activity, even at low concentrations, without showing any cytotoxicity.

Thus, the present invention provides a method of depigmenting and/or bleaching human skin, body hair or head hair, comprising applying to human skin, body hair or head hair at least one compound represented by formula (I):

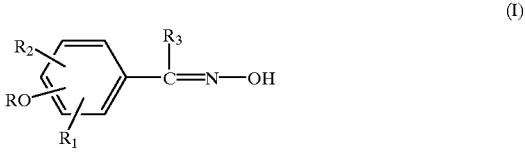

(I)

where
R represents a group chosen from:
a hydrogen atom;
a linear, branched or cyclic, saturated or unsaturated $C_1$–$C_{24}$ alkyl group, optionally hydroxylated with one or more hydroxyl functions;
an aryl group, which may be unsubstituted or substituted with one or more functions chosen from —OH; $NH_2$; —COOH; —$NO_2$; —$OR_5$ with $R_5$=$C_1$–$C_{24}$ alkyl; —$COOR_6$ with $R_6$=$C_1$–$C_{24}$ alkyl; —$NR_7R_8$ with $R_7$=H or $C_1$–$C_{24}$ alkyl, $R_8$=H or $C_1$–$C_{24}$ alkyl; and
a group —$COR_9$, $R_9$ representing a linear, branched or cyclic, saturated or unsaturated $C_1$–$C_{24}$ alkyl group, optionally hydroxylated with one or more hydroxyl functions, or an aryl group which may be unsubstituted or substituted with one or more functions chosen from —OH, —$NH_2$, —COOH, —$NO_2$, —$OR_5$, —$COOR_6$ and —$NR_7R_8$ in which $R_5$, $R_6$, $R_7$ and $R_8$ have the same definition as above;

$R_1$ and $R_2$, which may be identical or different, represent a group chosen from:
a hydrogen atom;
a linear, branched or cyclic, saturated or unsaturated $C_1$–$C_{24}$ alkyl group, optionally hydroxylated with one or more hydroxyl functions;
an aryl group, which may be unsubstituted or substituted with one or more functions chosen from —OH, —$NH_2$, —COOH, —$NO_2$, —$OR_5$, —$COOR_6$ and —$NR_7R_8$ in which $R_5$, $R_6$, $R_7$ and $R_8$ have the same definition as above;
a group chosen from: —OH; —$OQ_1$; —$COQ_2$; —$COOQ_3$; —$NQ_4Q_5$; —$CONQ_6Q_7$; —$SQ_8$; —$CH_2OQ_9$; $Q_1$, $Q_2$, $Q_3$, $Q_4$, $Q_5$, $Q_6$, $Q_7$, $Q_8$ and $Q_9$, which may be identical or different, being chosen from a hydrogen atom, linear, branched or cyclic, saturated or unsaturated $C_1$–$C_{24}$ alkyl groups, optionally substituted with one or more hydroxyl groups, aryl groups which may be unsubstituted or substituted with one or more functions chosen from: —OH, —$NH_2$, —COOH, —$NO_2$, —$OR_5$, —$COOR_6$ and —$NR_7R_8$ in which $R_5$, $R_6$, $R_7$ and $R_8$ have the same definition as above; and amino acid residues and cyclic or non-cyclic carbohydrate residues;

$R_3$ represents a group chosen from:
a hydrogen atom;
a linear, branched or cyclic, saturated or unsaturated $C_1$–$C_{24}$ alkyl group, optionally hydroxylated with one or more hydroxyl functions; and an aryl group, which may be unsubstituted or substituted with one or more functions chosen from —OH, —NH$_2$, —COOH, —NO$_2$, —OR$_5$, —COOR$_6$ and —NR$_7$R$_8$ in which R$_5$, R$_6$, R$_7$ and R$_8$ have the same definition as above.

A subject of the present invention is also the use of at least one compound of formula (I) above for the manufacture of a dermatological composition intended for depigmenting and/or bleaching human skin and/or for removing pigmentation marks from the skin and/or for depigmenting body hair and/or head hair, comprising a dermatologically acceptable medium and intended for topical application to the skin and/or its body hair or head hair.

Accordingly, the present invention provides a method of depigmenting and/or bleaching human skin, body hair or head hair, comprising applying to human skin, body hair or head hair at least one compound represented by formula (I).

The present invention also provides a cosmetic and/or dermatological composition, comprising a cosmetically and/or dermatologically acceptable carrier and at least one compound represented by formula (I).

The present invention also provides a method of making the cosmetic and/or dermatological composition.

A more complete appreciation of the invention and many of the attendant advantages thereof will be readily obtained as the same becomes better understood by reference to the following detailed description.

DETAILED DESCRIPTION OF THE INVENTION

Some of the compounds represented by formula (I) are described as photoprotective compounds intended for protecting the skin against light-induced ageing and solar erythema (WO 95/01157), as tyrosinase inhibitors in oral compositions for treating cancer, in combination with interferon (U.S. Pat. No. 4,762,705) or as lipoxygenase inhibitors, in anti-inflammatory compositions (U.S. Pat. No. 4,816,487). Each of these publications is incorporated herein by reference. However, these compounds have not been described as depigmenting agents or in depigmenting compositions.

These compounds have the advantage of being easy to synthesize. They can be obtained, for example, by reacting hydroxylamine with an aldehyde (aldoximes) or a ketone (ketoximes). The carbonyl reagent can optionally be used in acetal form.

Among the linear, saturated alkyl radicals containing from 1 to 24 carbon atoms which may be mentioned in particular are methyl, ethyl, propyl, butyl, hexyl, octyl, nonyl, dodecyl, hexadecyl, behenyl and octadecyl radicals. Among the branched saturated allyl radicals containing from 1 to 24 carbon atoms which may be mentioned in particular are isopropyl, tert-butyl, 2-ethylhexyl, 2-butyloctyl and 2-hexyldecyl radicals. Among the unsaturated alkyl radicals which may be mentioned more particularly is the allyl radical. When the alkyl radical is cyclic, mention may be made in particular of the cyclohexyl, cholesteryl or tert-butylcyclohexyl radical.

According to one preferred embodiment, the compounds of formula (I) of the present invention are those for which at least one of the conditions below is satisfied:

R=H or an alkyl group containing from 1 to 6 carbon atoms,

OR is in an ortho or para position relative to the oxime function,

R$_1$=R$_2$=H or OH or an alkyl group containing from 1 to 6 carbon atoms,

R$_3$=H or an alkyl group containing from 1 to 6 carbon atoms.

According to one particularly preferred embodiment, the compounds of formula (I) of the present invention are those for which at least one of the conditions below is satisfied:

R=H,

OR is in the para position relative to the oxime function,

R$_1$=R$_2$=H,

R$_3$ is an alkyl group containing from 1 to 6 carbon atoms, preferably a methyl group.

The preferred compound of formula (I) is para-hydroxyacetophenone oxime.

Relative to the compounds which are known as depigmenting agents, the compounds of formula (I) have the advantage of being more effective, as shown in the tests described below.

The composition according to the invention is suitable for topical use and thus contains a cosmetically or dermatologically acceptable medium, i.e., a medium which is compatible with the skin, body hair or head hair.

As one skilled in the art would readily appreciate, the amount of derivative of formula (I) in the composition according to the invention depends upon the desired effect and may, therefore, vary over a wide range. Advantageously, the derivative(s) of formula (I) will be present in the composition in an amount representing from 0.001 to 10% and preferably from 0.005 to 5% of the total weight of the composition. This range includes all specific values and subranges therebetween, such as 0.01, 0.05, 0.1, 0.5, 1, 2, 5 and 8% by weight.

The composition of the invention can be in any pharmaceutical form normally used for topical application, in particular in the form of an aqueous, aqueous-alcoholic or oily solution, an oil-in-water or water-in-oil or multiple emulsion, an aqueous or oily gel, a liquid, pasty or solid anhydrous product, a dispersion of oil in an aqueous phase with the aid of spherules, it being possible for these spherules to be polymer nanoparticles such as nanospheres and nanocapsules or, better still, lipid vesicles of ionic and/or nonionic type.

This composition can be more or less fluid and can have the appearance of white or colored cream, an ointinent, a milk, a lotion, a serum, a paste or a mousse. It can optionally be applied to the skin or the head hair in the form of an aerosol. It can also be in solid form and, for example, in the form of a stick. It can be used as a care product and/or as a make-up product. It can also be in the form of a shampoo or a conditioner.

The composition of the invention may also contain known adjuvants common in cosmetics and dermatology, such as hydrophilic or lipophilic gelling agents, hydrophilic or lipophilic active agents, preserving agents, antioxidants, solvents, fragrances, fillers, sunscreens, pigments, odor absorbers and dyestuffs. The amounts of these various adjuvants are those used conventionally in the fields under consideration, and, for example, from 0.01 to 20% of the total weight of the composition. Depending on their nature, these adjuvants can be introduced into the fatty phase, into the aqueous phase, into the lipid vesicles and/or into the nanoparticles.

As will be readily appreciated, those skilled in the art will take care to select these optional active or non-active adjuvants, and/or the amount thereof, such that the advantageous properties of the compounds according to the invention are not, or are not substantially, adversely affected by the addition envisaged.

When the composition of the invention is an emulsion, the proportion of the fatty phase can range from 5 to 80% by weight, and preferably from 5 to 50% by weight, relative to the total weight of the composition. The oils, emulsifiers and co-emulsifiers used in the composition in the form of an emulsion are chosen from those used conventionally in the field of use. The emulsifier and the co-emulsifier are present in the composition in a proportion ranging from 0.3 to 30% boy weight, and preferably from 0.5 to 20% by weight, relative to the total weight of the composition.

Examples of oils which can be used in the invention include mineral oils (liquid petroleum/jelly), oils of plant origin (avocado oil, soybean oil), oils of animal origin (lanolin), synthetic oils (perhydrosqualene), silicone oils (cyclomethicone) and fluoro oils (perfluoropolyethers). Fatty alcohols (cetyl alcohol), fatty acids and waxes (camauba wax, ozokerite) may also be used as fatty substances.

Emulsifiers and co-emulsifiers which can be used in the invention include, for example, fatty acid esters of polyethylene glycol, such as PEG-20 stearate, and fatty acid esters of glycerol, such as glyceryl stearate.

Examples of hydrophilic gelling agents include carboxyvinyl polymers (carbomer), acrylic copolymers such as acrylate/alkylacrylate copolymers, polyacrylamides, polysaccharides, natural gums and clays, and, as lipophilic gelling agents, mention may be made of modified clays such as bentones, metal salts of fatty acids, hydrophobic silica and polyethylenes.

Active agents which can be used in particular are polyols, vitamins, keratolytic agents and/or desquamating agents, anti-inflammatory agents, calmants and mixtures thereof. The compounds of formula (I) can also be combined with other depigmenting agents, such as kojic acid or hydroquinone and derivatives thereof, which allows these agents to be used in smaller doses. In the event of incompatibility, these active agents and/or the compounds of formula (I) can be incorporated into spherules, in particular ionic or non-ionic vesicles and/or nanoparticles (nanocapsules and/or nanospheres), so as to isolate them from each other in the composition.

UV screening agents with lipophilic or hydrophilic properties can also be used in these compositions, such as benzene-1,4bis(3-methylidene-camphorsulfonic acid), 2-ethylhexyl α-cyano-β,β-diphenylacrylate or octocrylene, butylmethoxydibenzoylmethane, octyl methoxycinnamate and/or titanium oxide and zinc oxide.

The composition of the invention is applied to human skin, body hair or head hair in order to provide a depigmenting and/or bleaching effect. The effect amount of the composition, and the amount of the compound represented by formula (I) in the composition, can be determined readily by methods routine to those skilled in the art. The composition is preferably applied topically to the area to be treated using well-known procedures. Body hair or head hair are advantageously treated using the composition of the present invention.

EXAMPLES

Having generally described this invention, a further understanding can be obtained by reference to certain specific examples which are provided herein for purposes of illustration only and are not intended to be limiting unless otherwise specified. The concentrations are given as percentages by weight.

Preparation of para-hydroxyacetophenone oxime 1.1 equivalents of hydroxylamine hydrochloride are added to a solution of para-hydroxyacetophenone in pyridine (16% dilution). The reaction mixture is maintained at reflux until the starting acetophenone has disappeared, and is then poured into ice-cold water. The medium is extracted with ethyl acetate. After drying, the organic phase is removed and the corresponding oxime is obtained quantitatively. The elemental analysis is in accordance with the structure.

Test:

A biological test demonstrated the depigmenting activity of the compounds of formula (I).

This test corresponds to the one described in patent FR 2 734 825 filed by the Applicant, as well as in the article by R. Schmidt, P. Krien and M. Régnier, Anal. Biochem., 235(2), 113–18, (1996). Both of these publications are incorporated herein by reference. This test is thus carried out on a co-culture of keratinocytes and melanocytes.

The $IC_{50}$ value, which corresponds to the micromolar ($\mu$M) concentration for which a 50% inhibition of melanogenesis is observed, is determined for each test compound.

Moreover, a grading is given to each of these compounds as regards their maximum depigmenting activity:

grade 1: 10 to 30% inhibition of melanogenesis relative to the control (same experiment without test compound);

grade 2: 30 to 60% inhibition of melanogenesis relative to the control (same experiment without test compound);

grade 3: 60 to 100% inhibition of melanogenesis relative to the control (same experiment without test compound).

The results are collated in the table below:

|  | Concentration | Grade |
| --- | --- | --- |
| Kojic acid | 500 $\mu$M | 2 |
| para-Hydroxyacetophenone | 1 $\mu$M | 1 |
| oxime | 10 $\mu$M | 2 |

In addition, the $IC_{50}$ value is 500 $\mu$M for kojic acid and 200 $\mu$M for para-hydroxyacetophenone oxime.

These compounds of formula (I) thus have greater depigmenting efficacy than kojic acid. In addition, they have the advantage of not being cytotoxic with regard to keratinocytes and melanocytes, which is a major defect of the depigmenting agents already known.

Examples of compositions

Example 1

| O/W emulsion | |
| --- | --- |
| Glyceryl stearate and PEG-100 stearate | 3% |
| Behenyl alcohol | 2.5% |
| Stearic acid | 1.5% |
| Beeswax | 4% |
| Caprylic/capric triglycerides | 7% |
| Hydrogenated polyisobutene | 12% |
| Polyacrylamide/$C_{13-14}$ isoparaffin/ laureth-7 (Sepigel 305) | 0.5% |
| Glycerol | 5% |
| UV screening agents | 7% |
| Preserving agents | 0.5% |
| para-Hydroxyacetophenone oxime | 0.5% |
| Demineralized water      qs | 100% |

When applied daily, the emulsion obtained makes it possible to bleach the skin.

Example 2

| Treatment fluid | |
|---|---|
| Diglycol/CHDM/isophthalates/SIP copolymer | 2% |
| Glycerol | 5% |
| Apricot oil | 14% |
| Cyclopentasiloxane | 6% |
| Preserving agents | 1% |
| UV screening agents | 7% |
| para-Hydroxyacetophenone oxime | 1% |
| Demineralized water | qs 100% |

The fluid obtained can be used daily and is capable of depigmenting the skin.

Example 3

| Treatment gel | |
|---|---|
| Glycerol | 5% |
| Acrylate/$C_{10}$—$C_{30}$ alkylacrylate copolymer (Pemulen TR2) | 0.5% |
| Preserving agents | 0.1% |
| Ethanol | 5% |
| UV screening agents | 7% |
| para-Hydroxyacetophenone oxime | 1% |
| Water | qs 100% |

When used on pigmentation marks, the gel obtained attenuates them or makes them disappear altogether.

Obviously, numerous modifications and variations of the present invention are possible in light of the above teachings. It is therefore to be understood that within the scope of the appended claims, the invention may be practiced otherwise than as specifically described herein.

This application is based on French Patent Application Ser. No. 99-00882, filed on Jan. 27, 1999, and incorporated herein by reference in its entirety.

What is claimed is:

1. A method of depigmenting or bleaching human skin, body hair or head hair or a combination thereof, comprising applying to human skin, body hair or head hair or a combination thereof at least one compound having the formula (I):

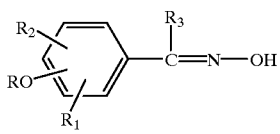

(I)

wherein:
R is a group selected from the group consisting of
hydrogen;
linear, branched or cyclic, saturated or unsaturated $C_1$–$C_{24}$ alkyl, which is optionally hydroxylated with one or more hydroxyl groups;
aryl, which is optionally substituted with one or more groups selected from the group consisting of —OH, $NH_2$, —COOH, —$NO_2$, —$OR_5$, wherein $R_5$ is $C_1$–$C_{24}$ alkyl, —$COOR_6$, wherein $R_6$ is $C_1$–$C_{24}$ alkyl, and —$NR_7R_8$, wherein $R_7$ is H or $C_1$–$C_{24}$ alkyl, and $R_8$ is H or $C_1$–$C_{24}$ alkyl; and
—$COR_9$, wherein $R_9$ is a linear, branched or cyclic, saturated or unsaturated $C_1$–$C_{24}$ alkyl, which is optionally hydroxylated with one or more hydroxyl groups; or aryl, which is optionally substituted with one or more groups selected from the group consisting of —OH, —$NH_2$, —COOH, —$NO_2$, —$OR_5$, —$COOR_6$, and —$NR_7R_8$, wherein $R_5$, $R_6$, $R_7$ and $R_8$ are as defined above;

$R_1$ and $R_2$, which are identical or different, each individually represent a group selected from the group consisting of
hydrogen;
linear, branched or cyclic, saturated or unsaturated $C_1$–$C_{24}$ alkyl, which is optionally hydroxylated with one or more hydroxyl groups;
aryl, which is optionally substituted with one or more groups selected from the group consisting of —OH, —$NH_2$, —COOH, —$NO_2$, —$OR_5$, —$COOR_6$, and —$NR_7R_8$, wherein $R_5$, $R_6$, $R_7$ and $R_8$ are as defined above;
a group selected from the group consisting of —OH, —$OQ_1$, —$COQ_2$, —$COOQ_3$, —$NQ_4Q_5$, —$CONQ_6Q_7$, —$SQ_8$, —$CH_2OQ_9$, wherein $Q_1$, $Q_2$, $Q_3$, $Q_4$, $Q_5$, $Q_6$, $Q_7$, $Q_8$ and $Q_9$, which are identical or different, are selected from the group consisting of hydrogen, linear, branched cyclic, saturated, and unsaturated $C_1$–$C_{24}$ alkyl groups, optionally substituted with one or more hydroxyl groups, aryl groups which are optionally substituted with one or more groups selected from the group consisting of —OH, —$NH_2$, —COOH, —$NO_2$, —$OR_5$, —$COOR_6$, and —$NR_7R_8$, wherein $R_5$, $R_6$, $R_7$ and $R_8$ are as defined above; and
amino acid residues and cyclic or non-cyclic carbohydrate residues; and $R_3$ is a group selected from the group consisting of
hydrogen,
linear, branched or cyclic, saturated or unsaturated $C_1$–$C_{24}$ alkyl, which is optionally hydroxylated with one or more hydroxyl groups, and
aryl, which is optionally substituted with one or more groups selected from the group consisting of —OH, —$NH_2$, —COOH, —$NO_2$, —$OR_5$, —$COOR_6$, and —$NR_7R_8$, wherein $R_5$, $R_6$, $R_7$ and $R_8$ are as defined above.

2. The method of claim 1, wherein at least one of the following conditions is satisfied:
R=H or alkyl containing from 1 to 6 carbon atoms,
OR is in an ortho orpara position relative to the oxime group,
$R_1=R_2=H$ or OH or allyl containing from 1 to 6 carbon atoms, or
$R_3=H$ or an alkyl group containing from 1 to 6 carbon atoms.

3. The method of claim 2, wherein at least one of the following conditions is satisfied:
R=H,
OR is in the para position relative to the oxime group,
$R_1=R_2=H$, or
$R_3=CH_3$.

4. The method of claim 3, wherein the compound having formula (I) is para-hydroxyacetophenone oxime.

5. The method of claim 1, wherein the compound having the formula (I) comprises 0.001 to 10% of the total weight of the composition.

6. The method of claim 1, wherein the compound having the formula (I) comprises 0.005 to 5% of the total weight of the composition.

7. The method of claim 1, wherein the at least one compound of the formula (I) is in a composition which further comprises at least one active agent selected from the group consisting of keratolytic agents, desquamating agents, UV screening agents, and other depigmenting agents.

8. The method of claim 1, wherein the composition is applied to human skin.

9. The method of claim 1, wherein the composition is applied to human body hair.

10. The method of claim 1, wherein the composition is applied to human head hair.

11. The method of claim 1, wherein the composition is in a form of an emulsion having a proportion of fatty phase ranging from 5 to 80% by weight based on the total weight of the composition.

12. The method of claim 7, wherein the at least one active agent and the at least one compound of the formula (I) are each isolated from the other in the composition by incorporation into capsules and spherules.

13. The method of claim 12, wherein said capsules or spherules are nanocapsules or nanospheres, respectively.

* * * * *

UNITED STATES PATENT AND TRADEMARK OFFICE
CERTIFICATE OF CORRECTION

PATENT NO. : 6,228,350 B1
DATED : May 8, 2001
INVENTOR(S) : Tuloup et al.

It is certified that error appears in the above-identified patent and that said Letters Patent is hereby corrected as shown below:

Column 8,
Line 48, delete "ortho orpara", should be -- ortho or para --;
Line 50, delete "allyl", should be -- alkyl --.

Signed and Sealed this

Thirteenth Day of November, 2001

Attest:

NICHOLAS P. GODICI
Attesting Officer
Acting Director of the United States Patent and Trademark Office